(12) United States Patent
Sakurada et al.

(10) Patent No.: US 9,888,847 B2
(45) Date of Patent: Feb. 13, 2018

(54) OPHTHALMIC EXAMINATION SYSTEM

(71) Applicant: TOPCON CORPORATION, Itabashi-ku (JP)

(72) Inventors: Tomohiro Sakurada, Itabashi-ku (JP); Yukio Ikezawa, Itabashi-ku (JP)

(73) Assignee: TOPCON CORPORATION, Itabashi-ku (JP)

( * ) Notice: Subject to any disclaimer, the term of this patent is extended or adjusted under 35 U.S.C. 154(b) by 0 days.

(21) Appl. No.: 15/334,817

(22) Filed: Oct. 26, 2016

(65) Prior Publication Data
US 2017/0127942 A1 May 11, 2017

(30) Foreign Application Priority Data

Nov. 10, 2015 (JP) .................................. 2015-220677

(51) Int. Cl.
| | | |
|---|---|---|
| *A61B 3/02* | (2006.01) | |
| *A61B 3/00* | (2006.01) | |
| *A61B 3/18* | (2006.01) | |
| *A61B 90/00* | (2016.01) | |
| *A61B 3/028* | (2006.01) | |
| *A61B 5/00* | (2006.01) | |

(52) U.S. Cl.
CPC .............. *A61B 3/18* (2013.01); *A61B 3/0008* (2013.01); *A61B 3/0033* (2013.01); *A61B 3/0041* (2013.01); *A61B 3/0091* (2013.01); *A61B 3/028* (2013.01); *A61B 5/0022* (2013.01); *A61B 5/7405* (2013.01); *A61B 90/361* (2016.02)

(58) Field of Classification Search
USPC ................................ 351/237–246, 222, 223
See application file for complete search history.

(56) References Cited

U.S. PATENT DOCUMENTS

| | | | | |
|---|---|---|---|---|
| 7,329,003 | B2 * | 2/2008 | Nicolini | ............... A61B 3/0083 108/43 |
| 9,693,687 | B2 * | 7/2017 | Tsuri | ........................ A61B 3/18 |
| 2005/0012896 | A1 | 1/2005 | Fukuma et al. | |

(Continued)

FOREIGN PATENT DOCUMENTS

| | | |
|---|---|---|
| JP | 2001-286442 | 10/2001 |
| JP | 2002-10978 | 1/2002 |
| JP | 2002-78679 | 3/2002 |

(Continued)

*Primary Examiner* — Mohammed Hasan
(74) *Attorney, Agent, or Firm* — Oblon, McClelland, Maier & Neustadt, L.L.P.

(57) ABSTRACT

According to an ophthalmic examination system of an embodiment, a user interface of an examination instruction apparatus is used to enter an instruction for examination. A first communication unit sends the instruction to an ophthalmic examination apparatus in real time. An examination optical system of the ophthalmic examination apparatus includes an optical element applied to an eye and a projection system that projects an examination light beam onto the eye through the optical element. An information presentation optical system includes a display and a light guide system that guides a display light beam from the display to the eye through the optical element. A second communication unit receives the instruction from the examination instruction apparatus. A controller displays the instruction received by the second communication unit on the display in real time.

13 Claims, 8 Drawing Sheets

(56) References Cited

U.S. PATENT DOCUMENTS

2005/0264760 A1 12/2005 Ikezawa
2007/0052927 A1* 3/2007 Noda .................. A61B 3/0025
                                                351/239

FOREIGN PATENT DOCUMENTS

| JP | 2002-78681 | 3/2002 |
| JP | 2005-342042 | 12/2005 |
| WO | WO 03/041572 A1 | 5/2003 |

* cited by examiner

OPHTHALMIC EXAMINATION SYSTEM

CROSS-REFERENCE TO RELATED APPLICATION

This application is based upon and claims the benefit of priority from Japanese Patent Application No. 2015-220677, filed Nov. 10, 2015; the entire contents of which are incorporated herein by reference.

FIELD

Embodiments described herein relate generally to an ophthalmic examination system.

BACKGROUND

An ophthalmic examination apparatus is used for the examination (measurement of properties, imaging, etc.) of an eye in medical institutions, optician's stores, health check and screening venues, patient's home, and the like. Typical examples of the ophthalmic examination apparatus include the followings.
  Visual acuity test apparatus for measuring visual acuity based on a response to a visual target presented
  Eye refraction test apparatus (refractometer, keratometer) for measuring the refractive properties of the eye
  Tonometer for measuring the intraocular pressure
  Specular microscope for obtaining the properties of the cornea (corneal thickness, cell distribution, etc.)
  Wavefront analyzer for obtaining the aberration information of the eye by using a Hartmann-Shack sensor
  Perimeter and micro-perimeter for the detection of visual field defects
  Optical coherence tomography (OCT) for obtaining cross-sectional images, three-dimensional data, analysis data, and the like of the fundus, the anterior segment, and the like of the eye using the optical interference
  Fundus camera for photographing the fundus
  Scanning laser ophthalmoscope (SLO) for capturing images of the fundus by laser scanning using a confocal optical system
  Multifunctional apparatus having a combination of two or more functions It is often the case that the examiner instructs a subject and operates the ophthalmic examination apparatus during an eye examination. In recent years, remote examination has been becoming popular. In the remote examination, the examiner, who is not present at the place where the ophthalmic examination apparatus is installed, conducts the examination while providing instructions for the subject and the ophthalmic examination apparatus (for example, see Patent Documents 1-6 listed below). The instructions for the subject include visual instructions and auditory instructions.
  Patent Document 1: Japanese Unexamined Patent Application Publication No. 2001-286442
  Patent Document 2: Japanese Unexamined Patent Application Publication No. 2002-10978
  Patent Document 3: Japanese Unexamined Patent Application Publication No. 2002-78679
  Patent Document 4: Japanese Unexamined Patent Application Publication No. 2002-78681
  Patent Document 5: Japanese Unexamined Patent Application Publication No. 2005-342042
  Patent Document 6: International Publication No. WO2003/041572

The ophthalmic examination apparatus performs examination by projecting light onto the subject's eye. For example, a visual target such as a Landolt ring is projected on the fundus in a visual acuity test, ring light is projected on the fundus or cornea in an eye refraction test, measuring light is projected on the fundus or cornea in OCT, and illumination light is projected on the fundus in the fundus photography. In many conventional remote examinations, the subject cannot receive visual instructions from the examiner without changing the orientation of his/her face or line of sight. This often interferes with a smooth progress of the test and the appropriate conveyance of instructions related to the visual target or the like. In addition, in the conventional remote examinations, it is not possible to provide interactive communication in which the subject feels as if the examiner is beside him/her.

SUMMARY

Embodiments are intended to realize the remote examination of the eye in which a subject can have interactive communication with the examiner without changing the orientation of his/her face or line of sight.

According to one embodiment, an ophthalmic examination system includes a plurality of ophthalmic examination apparatuses and an examination instruction apparatus. The examination instruction apparatus is used by an examiner to send instructions for examination to one of the ophthalmic examination apparatuses. The examination instruction apparatus includes a user interface and a first communication unit. The user interface is used to enter an instruction for examination. The first communication unit is configured to send the instruction entered by using the user interface to one of the ophthalmic examination apparatuses in real time. Each of the ophthalmic examination apparatuses includes an examination optical system, an information presentation optical system, a second communication unit, and a controller. The examination optical system includes an optical element applied to an eye, and a projection system configured to project an examination light beam for examining the eye onto the eye through the optical element. The information presentation optical system includes a display, and a light guide system configured to guide a display light beam output from the display to the eye through the optical element. The second communication unit is configured to receive the instruction sent from the examination instruction apparatus. The controller is configured to display the instruction received by the second communication unit on the display in real time.

According to one embodiment, it is possible to realize the remote examination of the eye in which a subject can have interactive communication with the examiner without changing the orientation of his/her face or line of sight.

DETAILED DESCRIPTION

Figure 1:
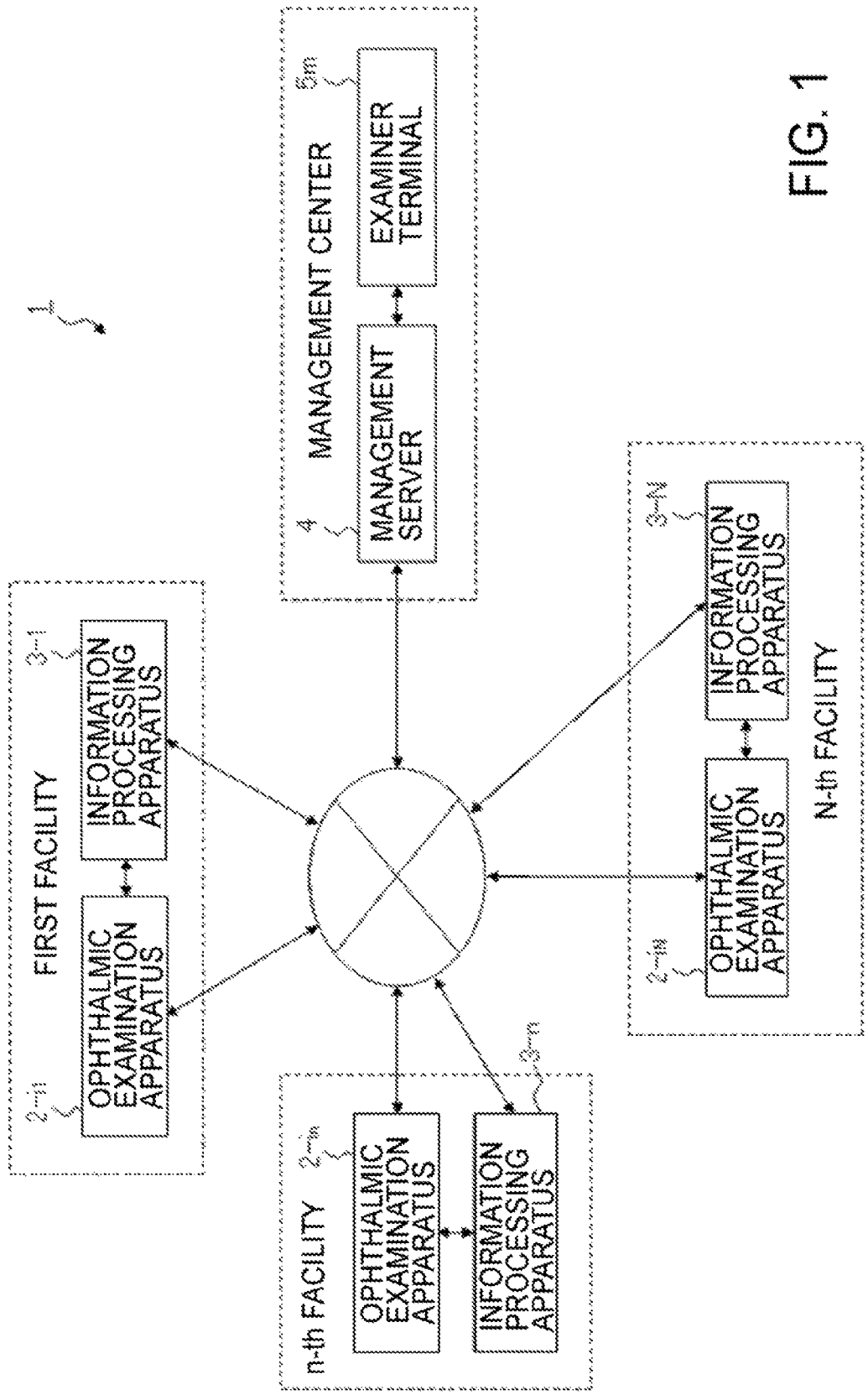
FIG. 1 is a schematic diagram illustrating an example of the configuration of an ophthalmic examination system according to an embodiment.

Referring now to the drawings, exemplary embodiments of the present invention are described below. All publications referred to herein and any known technology are hereby incorporated by reference in their entireties.

According to one embodiment, an ophthalmic examination system is applied to remote examination by using an ophthalmic examination apparatus installed in various facilities or a portable ophthalmic examination apparatus. In the remote examination, generally, the examiner uses an information processing apparatus (examiner terminal) installed in a facility (management center) that manages a plurality of ophthalmic examination apparatuses, and sends instructions to a subject who is undergoing an examination by using an ophthalmic examination apparatus. The subject can proceed with the examination based on the instructions.

Examples of the facilities where the ophthalmic examination apparatus is installed include medical institutions, optician's stores, health check and screening venues, patient's home, welfare facilities, public facilities, and the like. Further, the instructions sent from the examiner to the subject may include assistance (support) to the subject about how to proceed with the examination, how to use the ophthalmic examination apparatus, advices to the subject, and the like.

Note that, the aspects of the remote examination are not limited to those described above. For example, the instructions may be sent from an examiner terminal installed in a place other than the management center (e.g., the examiner's home) to the ophthalmic examination apparatus via the management center.

The ophthalmic examination apparatus may be any apparatus used in the examination of the eye, and may have the function of at least one of an ophthalmic measurement apparatus and an ophthalmologic imaging apparatus. The ophthalmic measurement apparatus is an apparatus for measuring the properties of the subject's eye. Examples of the ophthalmic measurement apparatus include visual acuity test apparatus (visual target presenting apparatus, phoropter, etc.), eye refraction test apparatus (refractometer, keratometer, etc.), tonometer, specular microscope, wave front analyzer, perimeter, micro perimeter, and the like. The ophthalmologic imaging apparatus is an apparatus for imaging the subject's eye. Examples of the ophthalmologic imaging apparatus include OCT, fundus camera, SLO, and the like. The ophthalmic examination apparatus may be provided with an application software for analyzing measurement data, captured images, or the like.

<Configuration of the Ophthalmic Examination System>

Described below is an example of the configuration of the ophthalmic examination system according to an embodiment. An ophthalmic examination system 1 illustrated in FIG. 1 as an example is configured by using a network that connects the management center and each of N facilities (first to N-th facilities) in which examination is performed.

Each of the facilities (n-th facility: n=1 to N, N is an integer 1 or larger) is provided with ophthalmic examination apparatus(es) 2-$i_n$ ($i_n$=1 to $K_n$, $K_n$ is an integer 1 or larger). This means that, in each facility (n-th facility), one or more ophthalmic examination apparatus(es) 2-$i_n$ is/are installed. The ophthalmic examination apparatus 2-$i_n$ constitutes a part of the ophthalmic examination system 1. Incidentally, the ophthalmic examination system 1 may include an examination apparatus capable of examination other than ophthalmic examination.

The ophthalmic examination apparatus 2-$i_n$ of this example have the function of an "examination apparatus" that performs the examination of the subject (subject's eye), and the function of a "computer" that performs various types of data processing and communicates with external devices. For another example, the examination apparatus and the computer may be provided separately. In this case, the examination apparatus and the computer may be capable of communicating with each other. Further, there may be arbitrary number of examination apparatuses and arbitrary number of computers. For example, there may be a single computer and a plurality of examination apparatuses.

Each facility (n-th facility) is further provided with an information processing apparatus 3-$n$. Incidentally, the ophthalmic examination system 1 need not necessarily include the information processing apparatus. The information processing apparatus 3-$n$ is a computer for use in the facility, and may be a mobile terminal such as a tablet computer or a smartphone, a server installed in the facility (in-house server, etc.), or the like. The information processing apparatus 3-$n$ is only required to be a computer having a function which can be used in the facility. The information processing apparatus 3-$n$ may be, for example, a computer (cloud server, etc.) installed in a place other than the facility.

The ophthalmic examination apparatus 2-$i_n$ and the information processing apparatus 3-$n$ may be capable of communicating with each other through a network built in the n-th facility (in-house LAN, etc.), a wide area network (the Internet, etc.), near-field communication technology, or the like.

A management server 4 is installed in the management center. The management server 4 can communicate with an examiner terminal(s) 5$m$ (m=1 to M, M is an integer 1 or larger) installed in (or outside) the management center via a network (LAN, wide area network, etc.). Further, the management server 4 can communicate with the ophthalmic examination apparatus 2-$i_n$ installed in each facility via a wide area network.

The management server 4 has the functions of, for example, relaying communication between the ophthalmic examination apparatus 2-$i_n$ and the examiner terminal 5$m$ and recording the contents of the communication. In addition, the management server 4 is provided with the function of associating the ophthalmic examination apparatus 2-$i_n$ with the examiner terminal 5$m$, i.e., assigning an examiner to each of the ophthalmic examination apparatuses 2-$i_n$. The management server 4 may be configured to detect the occurrence of a predetermined error in the contents of the communication between the ophthalmic examination apparatus $2\text{-}i_n$ and the examiner terminal $5m$, and notify the examiner terminal $5m$ or the like of a warning as well as recording it.

The examiner terminal $5m$ includes a computer that is used by the examiner to lead and manage the examination performed with the ophthalmic examination apparatus $2\text{-}i_n$.

<Configuration of the Ophthalmic Examination Apparatus>

A description is given of an example of the configuration of the ophthalmic examination apparatus $2\text{-}i_n$. The ophthalmic examination apparatus illustrated in FIG. 2 as an example corresponds to each of the ophthalmic examination apparatuses $2\text{-}i_n$ illustrated in FIG. 1. Similarly, each of the information processing apparatuses $3\text{-}n$ may sometimes be referred to as "information processing apparatus 3", and each of the examiner terminals $5m$ may sometimes be referred to as "examiner terminal 5".

The ophthalmic examination apparatus 2 includes a controller 20, an examination unit 21, an examination status information generating unit 22, a user interface (UI) 23, and a communication unit 24. These constituent elements may be integrally provided (i.e., in a single housing), or distributed in two or more housings. Examples of the former include refractometer, keratometer, tonometer, specular microscope, wave front analyzer, perimeter, micro perimeter, OCT, fundus camera, SLO, and the like. Examples of the latter include visual acuity test apparatus that includes a visual target presenting apparatus and a phoropter. Besides, a part or whole of the controller 20 may be implemented by a personal computer, a portable terminal, or the like. Further, a part or whole of the user interface 23 may be implemented by a personal computer, a portable terminal, a television receiver, a smart TV, or the like.

<Controller 20>

The controller 20 performs various types of control and operations. The controller 20 includes a processor. The "processor" as used herein is a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). For example, the controller 20 reads a program stored in a memory circuit or a storage device and executes it, thereby implementing the functions of the embodiment. The controller 20 may further include RAM, ROM, a hard disk drive, a solid state drive, and the like.

<Output Controller 201>

The controller 20 includes an output controller 201. The output controller 201 performs control for outputting the information sent to the ophthalmic examination apparatus 2 from the examiner terminal 5. Examples of the output information include visual information, audio information, and the like. The visual information is information recognized by the sensory system for vision, and includes text information, image information, and the like. The text information includes, for example, a text message that represents an instruction from the examiner. The image information includes, for example, a moving image of subject's face and hand, and a mark that represents an instruction from the examiner. The output controller 201 controls a liquid-crystal display (LCD) 214 and a display 231 (described later) to output the visual information. The audio information is information recognized by the sensory system for hearing, and includes warning sound, a voice message, and the like. The output controller 201 controls an audio output unit 233 (described later) to output the audio information. Specific examples of the processes performed by the output controller 201 are described later.

<Examination Unit 21>

The examination unit 21 performs the examination of the eye under control of the controller 20. The examination unit 21 has a configuration corresponding to the type of the ophthalmic examination apparatus 2. The configuration of the examination unit 21 may be at least a part of a known configuration, or may include a known configuration. The examination unit 21 includes optical systems as described below, and mechanisms (not illustrated) such as an actuator, a power transmission mechanism, and the like.

When the examination unit 21 has the function of measuring the properties of the subject's eye E, the examination unit 21 includes at least an optical system for projecting light onto the subject's eye, and may further includes an optical system for detecting the light projected onto the eye and returning therefrom, for example. In addition, the examination unit 21 may include optical systems for various kinds of functions such as an optical system for projecting a fixation target onto the eye, and an optical system for alignment, an optical system for focusing. The examination unit 21 may also include a processor for processing the detection result of the returning light (image signals, video signals, etc.).

When the examination unit 21 has the function of photographing the subject's eye E, the examination unit 21 includes, for example, an optical system for projecting light onto the subject's eye and an optical system for detecting the light projected onto the eye and returning therefrom. As in the case of measurement function, the examination unit 21 may include various kinds of optical systems. The examination unit 21 may also include a processor for processing the detection result of the returning light (image signals, video signals, etc.).

The optical systems as described above correspond to an examination optical system 211. The examination optical system 211 includes an optical element 212 and a projection system 213. The optical element 212 is applied to the subject's eye E to guide a light beam output from the projection system 213 to the subject's eye E. The optical element 212 may include any of various types of optical elements such as a lens (objective lens, etc.), a prism (objective prism, etc.), a concave mirror (parabolic mirror, etc.), a glass plate, and the like.

The projection system 213 projects the light beam for examining the subject's eye E (examination light beam) onto the subject's eye E through the optical element 212. The projection system 213 is provided with the LCD 214. The LCD 214 operates under the control of the controller 20. The LCD 214 has the functions of displaying information used for examination (examination information: visual target, fixation target, etc.) and displaying information received from the examiner terminal 5. The latter is a function of an information presenting optical system. The LCD 214 corresponds to a display of the information presenting optical system. The projection system 213 also implements the function of a light guide system that guides a light beam (display light beam), which corresponds to the information sent from the examiner terminal 5, from the LCD 214 to the subject's eye E through the optical element 212. That is, in the examination unit 21 of this embodiment, the examination optical system and the information presenting optical system are the same configuration. The examination optical system and the information presenting optical system may be configured separately, an example of which is described later.

<Examination Status Information Generating Unit 22>

The examination status information generating unit 22 generates examination status information indicating the status of the examination of the subject's eye E. The examination status information includes the progress status of examination (examination phase), on-going status (interim report) of examination (e.g., the history of visual targets having been presented in a visual acuity test), examination time (e.g., examination start time, elapsed time), or the like. When the ophthalmic examination apparatus 2 has the function of photographing the subject's eye E, the subject, or the like, the examination status information may include a captured image (still image, moving image) of the subject's eye E or the like. The examination status information may include audio information of the subject input via an audio input unit 234. The examination status information generated is sent to the examiner terminal 5, and is referred to by the examiner. The examination status information generating unit 22 includes, for example, a processor and a computer program for carrying out examination or a computer program for monitoring it.

The examination status information generating unit 22 need not necessarily process all the information sent from the ophthalmic examination apparatus 2 to the examiner terminal 5. For example, a moving image of the subject's eye E, the audio information of the subject, or the like can be directly sent to the examiner terminal 5. Thereby, the states of the subject's eye E, a request from the subject, or the like can be provided to the examiner substantially without a time lag.

<User Interface 23>

The user interface 23 has the function of outputting information for the subject (and the examiner nearby the subject), and the function for allowing the user to input information and provide operating instructions. The user interface 23 includes the display 231 and the audio output unit 233 for the former function, and an operation unit 232 and the audio input unit 234 for the latter function.

The display 231 includes a display device such as a flat panel display. The operation unit 232 includes operation devices such as buttons, keys, a joystick, knobs, and an operation panel provided on the cabinet or outside of the ophthalmic examination apparatus 2. The operation unit 232 may include operation devices (a mouse, a keyboard, a track pad, buttons, a touch panel, etc.) of a personal computer that is connected to the ophthalmic examination apparatus 2. The user interface 23 may include a device such as a touch panel obtained by integrating the display 231 and the operation unit 232, and a graphical user interface (GUI). The user interface 23 may include a computer program and a processor for implementing operation and input based on the subject's voice input from the audio input unit 234.

The audio output unit 233 includes, for example, a circuit for processing audio information (audio signals) to be output, and a speaker for outputting audio information processed. The audio input unit 234 includes a microphone for converting audio information into an electrical signal, and a circuit for processing the electrical signal.

<Communication Unit 24>

The communication unit 24 communicates data with the management server 4 and the information processing apparatus by an arbitrary communication system. For example, the communication unit 24 includes a communication interface conforming to the Internet, a communication interface conforming to LAN, a communication interface conforming to near field communication, and the like. Data communication can be performed either wirelessly or via a wired connection. The communication unit 24 may be capable of data communication with an external device other than the management server 4 and the information processing apparatus 3. Data sent and received by the communication unit 24 may be encrypted. In this case, for example, the controller 20 includes an encryptor that encrypts data to be sent, and a decoder that decodes data having been received.

<Configuration of the Information Processing Apparatus>

Figure 3:
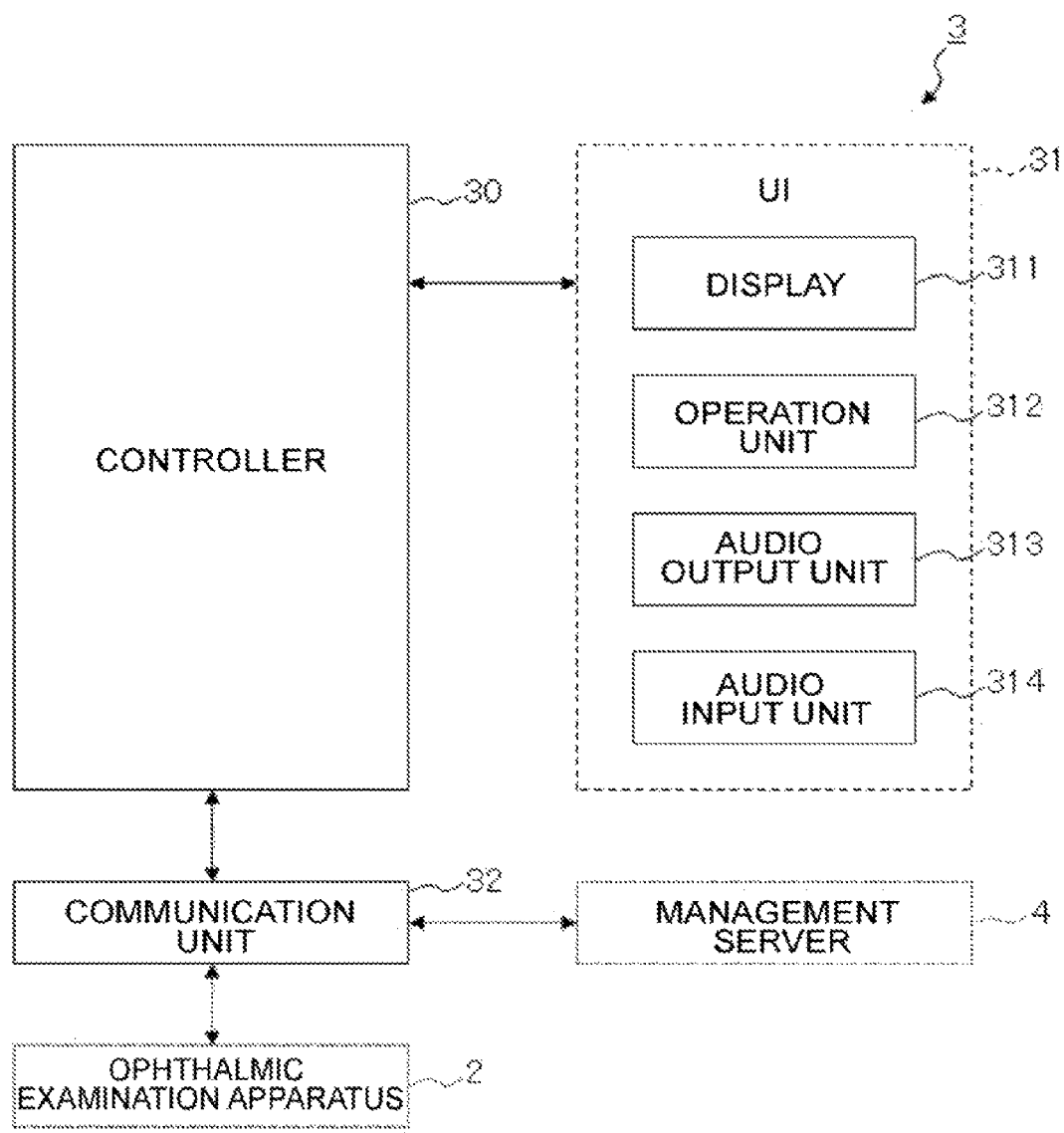
FIG. 3 is a schematic diagram illustrating an example of the configuration of the ophthalmic examination system of the embodiment.

A description is given of an example of the configuration of the information processing apparatus 3. The information processing apparatus 3 illustrated in FIG. 3 as an example includes a controller 30, a user interface (UI) 31, and a communication unit 32.

<Controller 30>

The controller 30 controls each unit of the information processing apparatus 3, and performs various types of arithmetic operations. The controller 30 includes a processor. The controller 30 may further include RAM, ROM, a hard disk drive, a solid state drive, and the like.

<User Interface 31>

The user interface 31 has the function of outputting information for a user, and the function for allowing the user to input information and provide operating instructions. As with the user interface 23 of the ophthalmic examination apparatus 2, the user interface 31 includes a display 311, an operation unit 312, an audio output unit 313, and an audio input unit 314.

<Communication Unit 32>

The communication unit 32 communicates data with the management server 4 and the ophthalmic examination apparatus 2. The data communication and encryption performed by the communication unit 32 may be the same as those performed by the communication unit 24 of the ophthalmic examination apparatus 2.

<Configuration of the Examiner Terminal>

Figure 4:
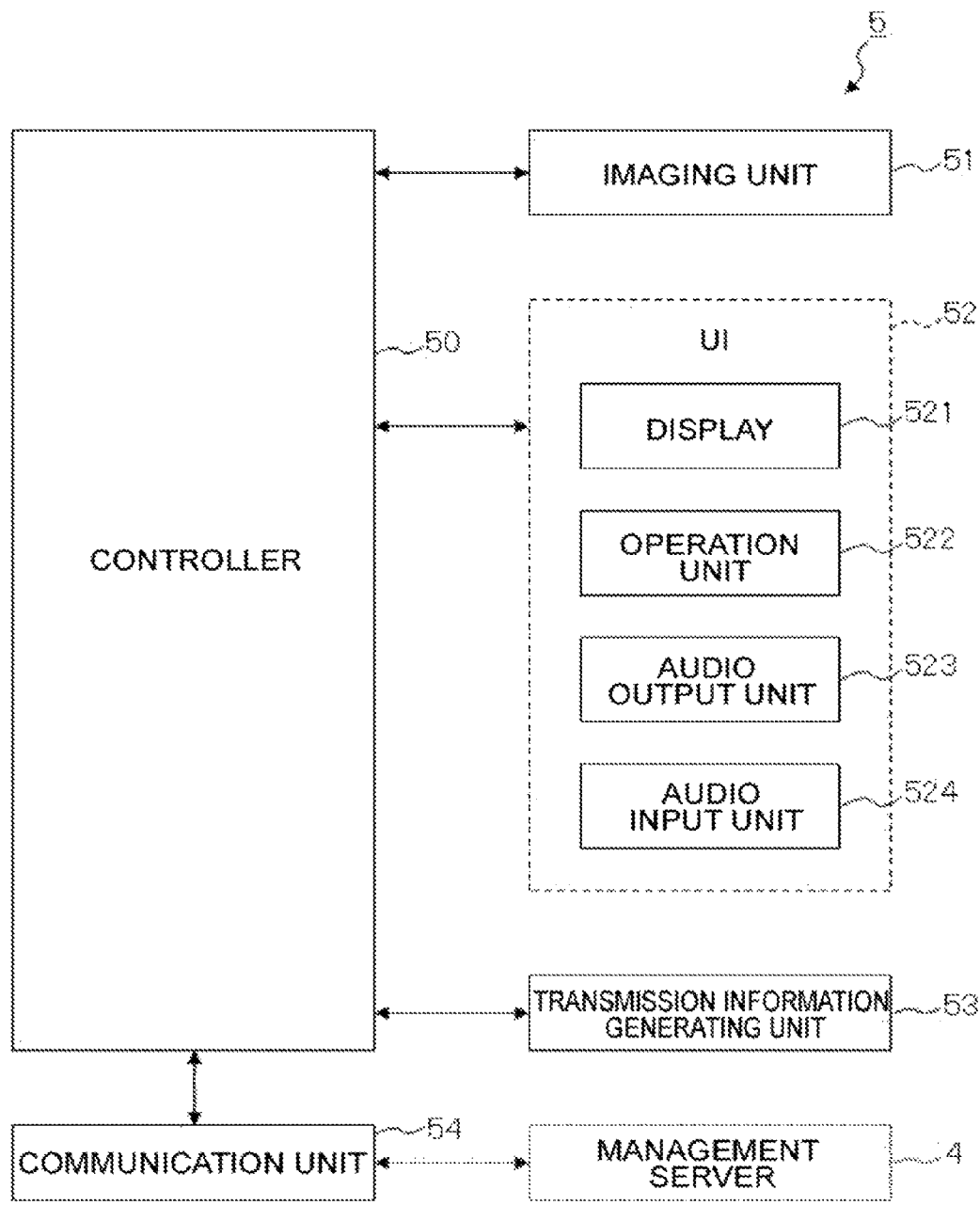
FIG. 4 is a schematic diagram illustrating an example of the configuration of the ophthalmic examination system of the embodiment.

A description is given of an example of the configuration of the examiner terminal 5. The examiner terminal 5 illustrated in FIG. 4 as an example includes a controller 50, an imaging unit 51, a user interface (UI) 52, a transmission information generating unit 53, and a communication unit 54.

<Controller 50>

The controller 50 controls each unit of the examiner terminal 5, and performs various types of arithmetic operations. The controller 50 includes a processor. The controller 50 may further include RAM, ROM, a hard disk drive, a solid state drive, and the like.

<Imaging Unit 51>

The imaging unit 51 is used to capture a moving image of the examiner, and includes, for example, a video camera. The object to be photographed includes a body part(s) (e.g., face, upper body, hand, etc.) used to provide an instruction to the subject.

<User Interface 52>

The user interface 52 has the function of outputting information for the examiner, and the function for allowing the examiner to input information and provide operating instructions. As with the user interface 23 of the ophthalmic examination apparatus 2, the user interface 52 includes a display 521, an operation unit 522, an audio output unit 523, and an audio input unit 524.

For example, the controller 50 controls the display 521 to display a screen (GUI, etc.) to present the examination status information successively sent from the ophthalmic examination apparatus 2 and to enter an instruction to the subject. In addition, the controller 50 controls the audio output unit 523 to output audio information of the subject. With reference to the display information and audio information, the examiner can determine the content of an instruction, and enter it by using the operation unit 522. Meanwhile, a voice instruction is entered through the audio input unit 524.

<Transmission Information Generating Unit 53>

Based on the content (instruction) that the examiner has entered using the user interface 52, the transmission information generating unit 53 generates information (transmission information) for the subject who uses the ophthalmic examination apparatus 2. The transmission information generating unit 53 includes, for example, a processor and a transmission information generating program to be executed in conjunction with the screen (GUI).

Note that the transmission information generating unit 53 need not necessarily process all the information sent from the examiner terminal 5 to the ophthalmic examination apparatus 2. For example, the moving image of the examiner, the audio information, or the like can be directly sent to the ophthalmic examination apparatus 2. Thereby, instructions from the examiner can be provide to the subject substantially without a time lag.

<Communication Unit 54>

The communication unit 54 communicates data with the management server 4. The data communication and encryption performed by the communication unit 54 may be the same as those performed by the communication unit 24 of the ophthalmic examination apparatus 2.

<Usage Mode>

Figure 5:
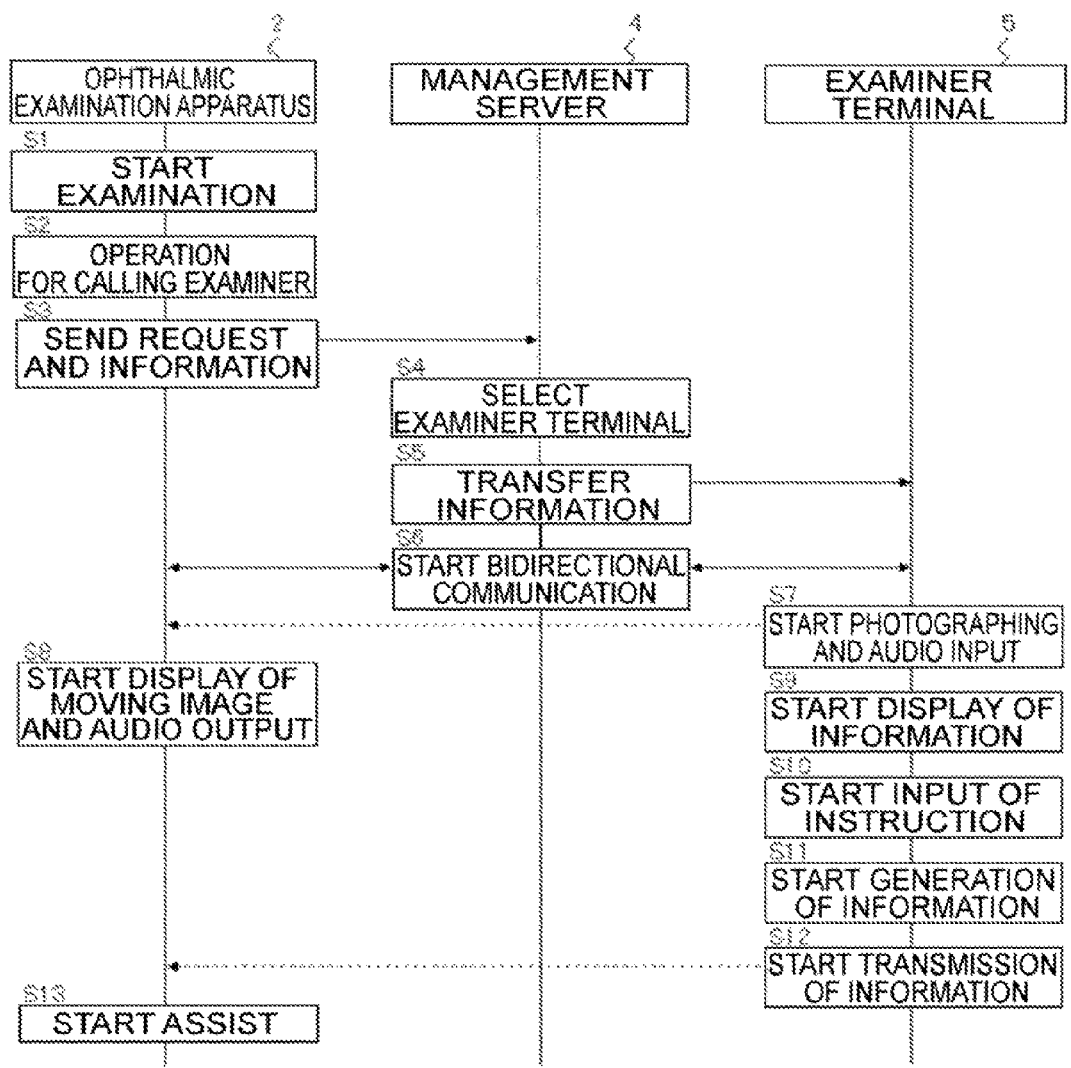
FIG. 5 is a sequence diagram illustrating an example of a usage mode of the ophthalmic examination system of the embodiment.

A description is given of a usage mode of the ophthalmic examination system of this embodiment. FIG. 5 illustrates an example of the usage mode.

(S1: Start Examination)

Examination of the subject's eye E using the ophthalmic examination apparatus 2 starts. The communication (bidirectional communication) between the ophthalmic examination apparatus 2 and the examiner terminal 5 may be started in this stage. In response to the start of the examination, the controller 20 controls the examination status information generating unit 22 to start generating the examination status information.

(S2: Request for Calling Examiner)

When needing assistance from the examiner, the subject calls the examiner by using the user interface 23. Examples of the case where the assist of the examiner is required include a case where the subject does not know how to conduct the examination, when he/she becomes tired, when he/she wants to return (redo) the steps of the examination. Examples of the way how the user uses the user interface 23 include performance of a predetermined operation with the operation unit 232, and input of voice with the audio input unit 234.

(S3: Send Request and Information)

The controller 20 controls the communication unit 24 to send the examiner call request input in step S2 to the management server 4 together with prescribed information. Examples of the information sent with the examiner call request include identification information assigned in advance to the ophthalmic examination apparatus 2 (apparatus ID), identification information assigned in advance to the subject (subject ID), identification information assigned in advance to a facility where the ophthalmic examination apparatus 2 is installed (facility ID), at least part of the examination status information generated at that point, the content of the examiner call request, and the like.

(S4: Select Examiner Terminal)

Having received the examiner call request and the information sent from the ophthalmic examination apparatus 2 in step S3, the management server 4 selects an examiner to assist the subject (i.e., select any one of the examiner terminals 5). To that end, the management server 4 has, for example, the function of monitoring the operating status of each of the examiner terminals 5. The management server 4 selects any one of the examiner terminals 5 that are not currently running (the examiners who are not currently performing assistance of subjects).

(S5: Transfer Information)

The management server 4 transfers the information received from the ophthalmic examination apparatus 2 to the examiner terminal 5 selected in step S4.

(S6: Start Bidirectional Communication)

Further, the management server 4 establishes bidirectional communication between the ophthalmic examination apparatus 2 that has sent the examiner call request and the like in step S3 and the examiner terminal 5 selected in step S4. At this time, the management server 4 may also establish communication between the information processing apparatus 3 and the examiner terminal 5. As described above, the communication may be established in the previous stage.

(S7: Start Photographing)

When the examiner terminal 5 receives the information transferred in step S5, the controller 50 controls the imaging unit 51 to start capturing a moving image of the examiner. At this time, input of voice coming out of the examiner is also started. Frames that the imaging unit 51 successively acquires are sent to the ophthalmic examination apparatus 2 in real time via the management server 4.

(S8: Start Display of Information)

The ophthalmic examination apparatus 2 receives the frames and audio information sequentially sent from the examiner terminal 5. The output controller 201 displays the frames in real time on the LCD 214. Thus, a moving image of the examiner is displayed in real time. The output controller 201 also controls the audio output unit 233 to output the audio information in real time. Thereby, the voice of the examiner is output in real time.

Through the cooperative operation as above, the subject can perceive the face, gestures, voice, and the like of the examiner in real time. On the other hand, the examiner can also perceive the voice, operation, and the like of the subject in real time.

(S9: Start Display of Information)

In order to facilitate the assist work by the examiner, the controller 50 of the examiner terminal 5 displays the screen (GUI, etc.) described above on the display 521, and displays the information transferred from the management server 4 in step S5 (especially, the examination status information) on the screen. Upon receipt of new examination status information, the controller 50 updates the display contents.

(S10: Start Input of Instruction)

The examiner enters an instruction using the operation unit 522 (GUI). Examples of the contents of the instruction include a change of examination, presentation of text information, presentation of image information, and the like. Besides, examples of instructions using means other than GUI include instructions by body language, instructions by voice, and the like. Specific examples of the instruction are described later.

(S11: Start Generation of Information)

Based on the contents (instruction) entered in step S10, the transmission information generating unit 53 generates transmission information for the subject. The transmission information is generated, for example, each time the examiner enters an instruction.

(S12: Start Transmission of Information)

The examiner terminal 5 sends the transmission information generated in step S11 to the ophthalmic examination apparatus 2 via the management server 4.

(S13: Start Assist)

The ophthalmic examination apparatus 2 receives the transmission information sent from the examiner terminal 5 in step S12. The output controller 201 displays the moving image and the instruction from the examiner on the LCD 214 based on the transmission information.

Described below is a specific example of the instruction for the examination. Here, it is assumed that a change of examination includes the operation of switching the type of the visual target used in the visual acuity test from a Landolt ring to an illustration chart. The illustration chart is a visual target made of illustrations. Specifically, for example, the illustration chart is a visual target in which a familiar scenery contains characters and images corresponding to several levels of visual acuity scores. An instruction to change examination is performed by, for example, operating a predetermined software key provided on the GUI. Having received the instruction to change the examination, the output controller 201 of the ophthalmic examination apparatus 2 switches the visual target for the visual acuity test displayed on the LCD 214 from a Landolt ring to the illustration chart.

Figure 6A:
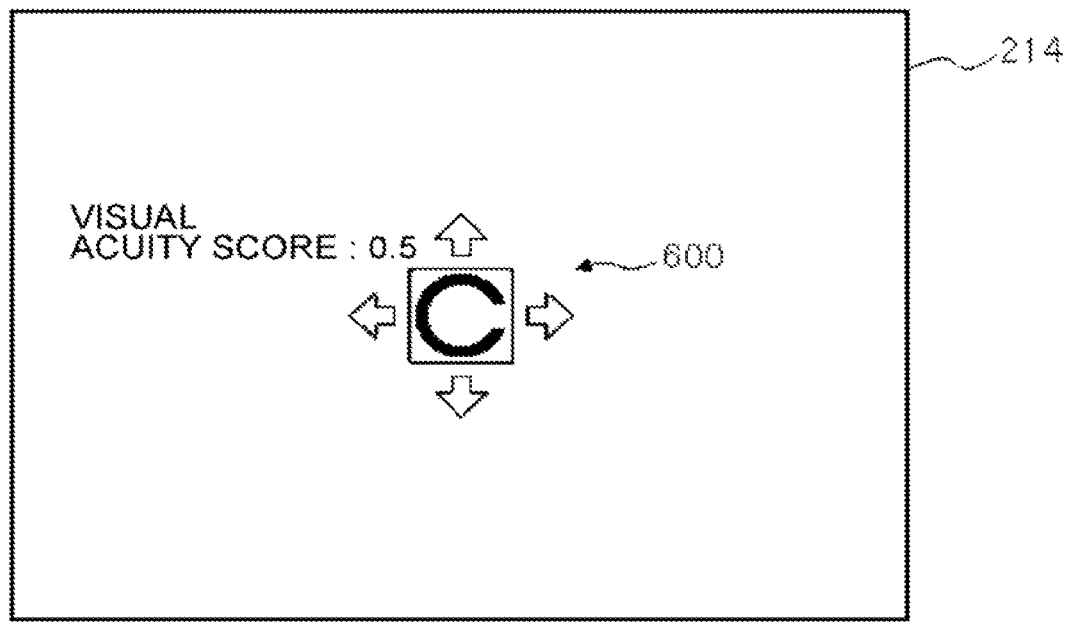
FIG. 6A is a schematic diagram for explaining a usage mode of the ophthalmic examination system of the embodiment.

FIG. 6A illustrates an example of display for visual acuity test using a Landolt ring. As illustrated in FIG. 6A, display content 600 includes a Landolt ring in a "C" shape, a character string "visual acuity: 0.5" representing the visual acuity score corresponding to the Landolt ring, and arrow images pointing up, down, left, and right directions, respectively, which are arranged around the Landolt ring to enter the selection of the direction of the gap in the Landolt ring.

Figure 6B:
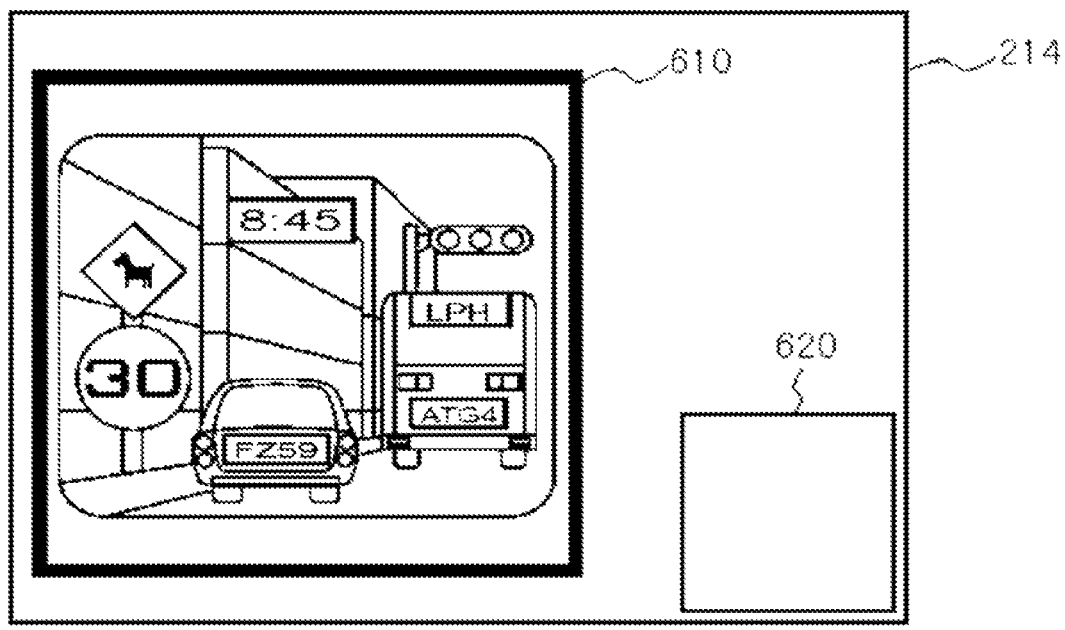
FIG. 6B is a schematic diagram for explaining a usage mode of the ophthalmic examination system of the embodiment.

FIG. 6B illustrates an example of display for visual acuity test using an illustration chart. In the example of FIG. 6B, an illustration chart 610 is displayed on the LCD 214. The illustration chart 610 illustrates an ordinary motor vehicle and a bus running on the road, a road sign, a digital clock, and the like. Speed limit "30" indicated by the road sign, the time "8:45" indicated by the digital clock, a character string "LPH" that represents the destination of the bus, a character string "ATG4" written on the license plate of the bus, a character string "FZ59" written on the license plate of the ordinary motor vehicle are in their respective sizes corresponding to different visual acuity scores. As illustrated in FIG. 6B, an examiner image display area 620 is also displayed. In the examiner image display area 620, a moving image of the examiner being acquired by the examiner terminal 5 is displayed in real time by the output controller 201.

Figure 6C:
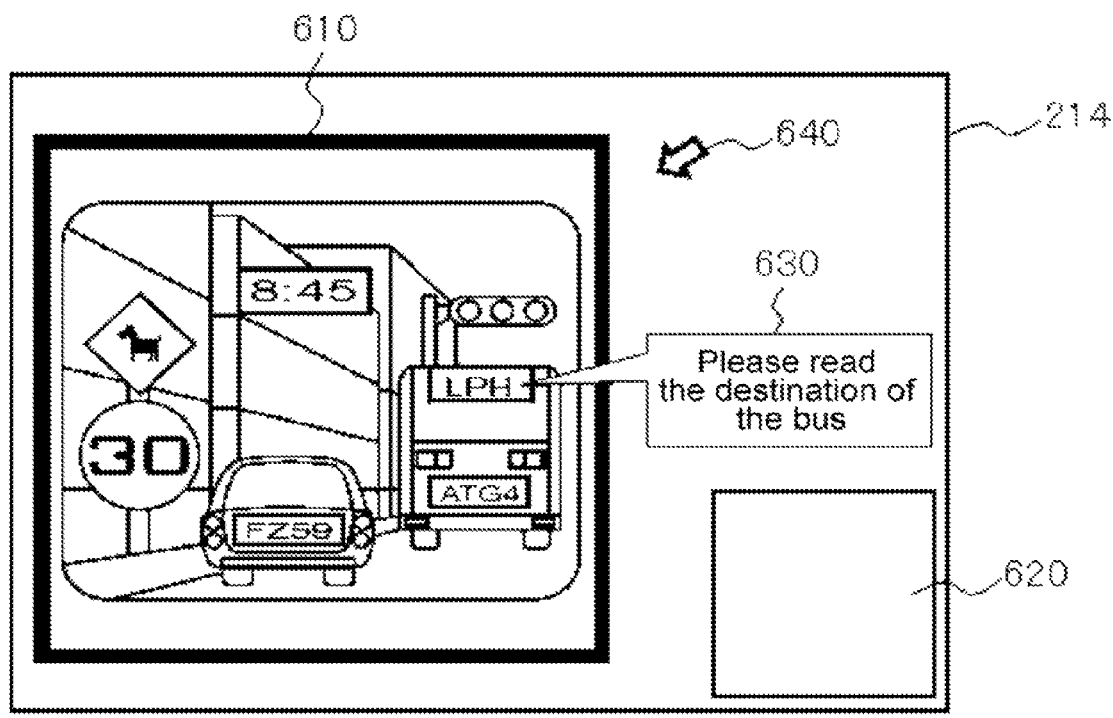
FIG. 6C is a schematic diagram for explaining a usage mode of the ophthalmic examination system of the embodiment.

FIG. 6C illustrates an example of display of an instruction from the examiner. For example, in order to make the subject read the character string "LPH" indicating the destination of the bus, the examiner performs an operation for that purpose using the GUI. The output controller 201 displays instruction information 630 that indicates the content of instruction based on transmission information sent from the examiner terminal 5. As the instruction information 630 of this example, a character string "please read the destination of the bus" is displayed. The instruction information 630 is a balloon image pointing the destination of the bus. The examiner can provide a voice instruction while displaying the instruction information 630.

If the information about the sight of the subject's eye E (visual acuity score, refractive power, etc.) is acquired in advance, the output controller 201 may adjust the display size of the instruction based on this information. The output controller 201 stores, in advance, table information in which the visual acuity scores and/or the refractive powers are associated with display sizes of character strings and/or display sizes of images. When the content of the instruction contains text information or image information, the output controller 201 selects a display size associated with the visual acuity score and/or the refractive power of the subject's eye E, and displays the text information or the image information in the display size selected on the LCD 214.

In the example of FIG. 6C, a pointer 640 is also displayed. The examiner can move the pointer 640 in real time using the GUI. Thereby, for example, the examiner can point the position of the destination display of the bus.

<Actions and Effects>

Described below are the actions and effects of the embodiment.

According to the embodiment, the ophthalmic examination system includes a plurality of ophthalmic examination apparatuses ($2\text{-}i_n$), and an examination instruction apparatus (the examiner terminal 5) used by an examiner to send instructions for examination to one (or more) of the ophthalmic examination apparatuses.

The examination instruction apparatus includes an imaging unit (51), a user interface (the user interface 52), a first communication unit (the communication unit 54). The imaging unit is configured to capture a moving image of the examiner. The user interface is used to enter an instruction for examination. The first communication unit is configured to send the moving image captured by the imaging unit and the instruction entered by using the user interface in real time to one of the ophthalmic examination apparatuses.

Each of the ophthalmic examination apparatuses includes an examination optical system (211), an information presentation optical system (the examination optical system 211), a second communication unit (the communication unit 24), and a controller (20). The examination optical system includes an optical element (212) to be applied to an eye, and a projection system (213) configured to project an examination light beam for examining the eye onto the eye through the optical element. The information presentation optical system includes a display (the LCD 214), and a light guide system (the projection system 213, the optical element 212, etc.) configured to guide a display light beam output from the display to the eye through the optical element. The second communication unit is configured to receive the moving image and the instruction sent from the examination instruction apparatus. The controller is configured to display the moving image and the instruction received by the second communication unit on the display in real time. The term "real time" as used herein can allow for at least a degree of time lag that does not interfere with the interactive communication between the subject and the examiner.

According to this embodiment, instructions and a moving image of the examiner are presented to the subject's eye through the optical element to be applied to the examination. Thus, the subject can have interactive communication with the examiner without changing the orientation of his/her face or line of sight.

In the above exemplary embodiment, at least part of the examination optical system and at least part of the information presentation optical system share a common configuration. In addition, the display displays examination information used in the examination of the subject's eye. The examination information may include a visual target (a Landolt ring, illustration chart, etc.) used for the visual acuity test of the subject's eye. The projection system of the examination optical system is configured to project an examination light beam output from the display, which is displaying the examination information, onto the subject's eye. When the second communication unit receives information including at least one of the moving image and the instruction, the controller controls the display to display the information received together with the examination information.

Figure 7:
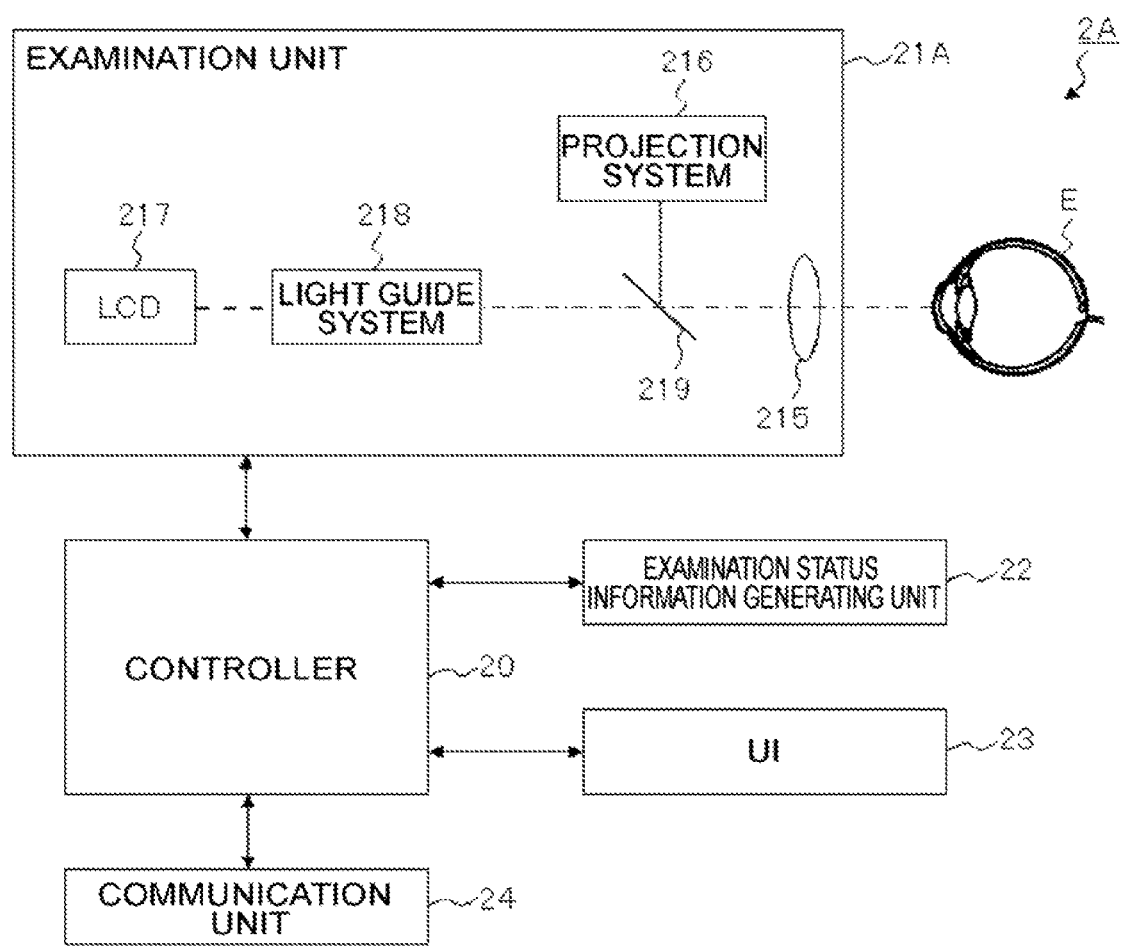
FIG. 7 is a schematic diagram illustrating an example of a configuration of an ophthalmic examination system according to a modification of the embodiment.

FIG. 7 illustrates an example in which the examination optical system and the information presentation optical system are arranged separately. In an examination unit 21A of an ophthalmic examination apparatus 2A, the examination optical system includes an optical element 215 applied to the subject's eye E, and a projection system 216 configured to project an examination light beam for examining the subject's eye E to the subject's eye E through the optical element 215. The information presentation optical system includes an LCD 217 (display), and a light guide system 218 configured to guide a display light beam output from the LCD 217 to the subject's eye E through the optical element 215. The optical path of the examination optical system and the optical path of the examination information presentation optical system are combined by a beam splitter 219. The beam splitter 219 may be, for example, a half mirror, a dichroic mirror, or a polarizing beam splitter. Incidentally, the configuration may be basically the same as that illustrated in FIG. 2 except the examination unit 21.

Figure 2:
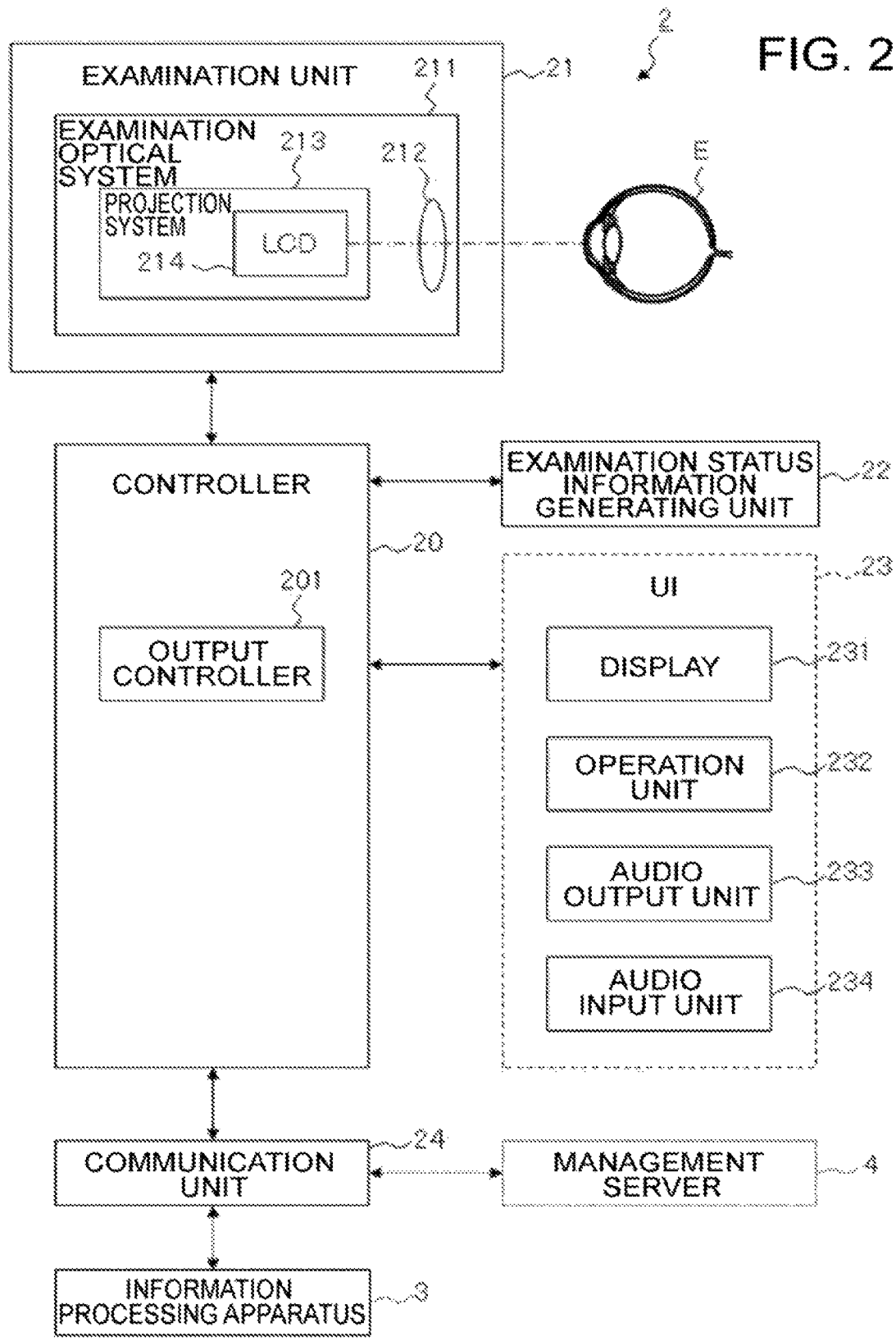
FIG. 2 is a schematic diagram illustrating an example of the configuration of the ophthalmic examination system of the embodiment.

Whether to configure the examination optical system and the information presentation optical system integrally as illustrated in FIG. 2 or configure them separately as illustrated in FIG. 7 is determined depending on, for example, the functions of the ophthalmic examination apparatus.

In embodiments, the controller of the ophthalmic examination apparatus may be configured to set the display size of instructions from the examiner based on at least one of the visual acuity score and refractive power of the eye obtained in advance. Incidentally, the examination instruction apparatus (examiner terminal), the management server, or the like can be configured to set the display size and send the setting information to the ophthalmic examination apparatus. The embodiment is construed as including such configurations.

With this configuration in which the display size of instructions is adjustable according to the visual acuity score and/or the refractive power of the subject's eye, the subject can correctly and easily recognize the contents of the instructions.

In embodiments, the controller of the ophthalmic examination apparatus may be configured to display at least one of text information and image information for supporting the examination of the subject's eye as the instruction from the examiner. Alternatively or additionally, if each of the ophthalmic examination apparatuses is provided with an audio output unit (the audio output unit 233) that outputs audio information, and if an instruction from the examiner includes audio information, the controller may control the audio output unit to output the audio information in real time. With this configuration, instructions can be provided to the subject in a variety of ways.

In embodiments, each of the ophthalmic examination apparatuses may include an input unit (the operation unit 232, the audio input unit 234, etc.) for inputting a message from the subject. The message may be in any form such as, for example, text information, image information, audio information, and the like. The second communication unit (the communication unit 24) is configured to send an input message to the examination instruction apparatus (the examiner terminal 5) in real time. The first communication unit (the communication unit 54) of the examination instruction apparatus is configured to receive the message sent from the ophthalmic examination apparatus. Further, the user interface (the display 521, the audio output unit 523, etc.) is configured to output the received message in real time.

With this configuration, the message from the subject can be sent to the examiner in real time. Thereby, the interactive communication between the two can be made more suitable.

In embodiments, each of the ophthalmic examination apparatuses may include an information generating unit (the examination status information generating unit 22) that generates examination status information indicating the status of the examination of the subject's eye. The second communication unit (the communication unit 24) is configured to send the examination status information to the examination instruction apparatus (the examiner terminal 5) in real time. The first communication unit (the communication unit 54) of the examination instruction apparatus is configured to receive the examination status information sent from the ophthalmic examination apparatus. The user interface (the display 521, etc.) is configured to output the received examination status information in real time.

With this configuration, the examiner can see the condition of the subject and the status of examination in real time. Thus, it is possible to provide more appropriate assistance.

The ophthalmic examination system of embodiments may include an information processing apparatus (3) that can be used in the vicinity of any of the ophthalmic examination apparatuses. The information processing apparatus is configured to receive information including at least one of the moving image and the instruction sent from the examination instruction apparatus (the examiner terminal 5) with a communication unit (the communication unit 32), and display the received information with a display (311) in real time.

With this configuration, instructions from the examiner can be provided to the person who assists the subject in the examination site. That is, the examiner who assists the subject from a remote location and a person who assists the subject in the examination site can share the instruction contents. Thereby, it is possible to provide more appropriate assistance.

In the above embodiments, both an instruction and a moving image of the examiner are provided to the subject; however, only an instruction from the examiner may be provided to the subject. In this case, the examiner terminal 5 need not include the imaging unit 51 in the constituent elements illustrated in FIG. 4. In addition, the examiner image display area 620 as illustrated in FIGS. 6B and 6C need not be displayed on the LCD 214. Further, the examiner terminal 5 may be provided with the imaging unit 51 such that whether or not to provide a moving image of the examiner can be arbitrarily determined. Described below is an exemplary embodiment in which at least an instruction from the examiner is provided to the subject.

The ophthalmic examination system of the embodiment includes a plurality of ophthalmic examination apparatuses (2-$i_n$) and an examination instruction apparatus (the examiner terminal 5) used by the examiner to send instructions for examination to one (or more) of the ophthalmic examination apparatuses.

The examination instruction apparatus includes a user interface (the user interface 52) and a first communication unit (the communication unit 54). The user interface is used to enter an instruction for examination. The first communication unit is configured to send an instruction entered by using the user interface to one of the ophthalmic examination apparatuses in real time. Incidentally, the examination instruction apparatus of this embodiment need not include the imaging unit (51).

On the other hand, each of the ophthalmic examination apparatuses includes an examination optical system (211), an information presentation optical system (the examination optical system 211), a second communication unit (the communication unit 24), and a controller (20). The examination optical system includes an optical element (212) to be applied to the subject's eye, and a projection system (213) configured to project an examination light beam for examining the subject's eye onto the subject's eye through the optical element. The information presentation optical system includes a display (the LCD 214), and a light guide system (the projection system 213, the optical element 212, etc.) configured to guide a display light beam output from the display to the subject's eye through the optical element. The second communication unit is configured to receive instructions sent from the examination instruction apparatus. The controller is configured to display, on the display, instructions received by the second communication unit in real time.

Input mode, transmission mode, reception mode, and output mode of examiner's instructions are each arbitral, and may be the same as at least the above embodiment.

In this embodiment also, instructions of the examiner can be provide to the subject's eye through the optical element applied to examination. Thus, the subject can have interactive communication with the examiner without changing the orientation of his/her face or line of sight.

The embodiments described above are mere examples for embodying or carrying out the present invention, and therefore susceptible to several modifications and variations (omission, substitution, addition, etc.), all coming within the scope of the invention.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic examination system, comprising:
a plurality of ophthalmic examination apparatuses; and
an examination instruction apparatus used by an examiner to send instructions for examination to one of the ophthalmic examination apparatuses, wherein
the examination instruction apparatus includes
a user interface used to enter an instruction for examination, and
a first communication unit configured to send the instruction entered by using the user interface to one of the ophthalmic examination apparatuses in real time, and
each of the ophthalmic examination apparatuses includes
an examination optical system including an optical element applied to an eye, and a projection system configured to project an examination light beam for examining the eye onto the eye through the optical element,
an information presentation optical system including a display, and a light guide system configured to guide a display light beam output from the display to the eye through the optical element,
a second communication unit configured to receive the instruction sent from the examination instruction apparatus, and
a controller configured to display the instruction received by the second communication unit on the display in real time.

2. The ophthalmic examination system of claim 1, wherein
the examination instruction apparatus further includes an imaging unit configured to capture a moving image of the examiner,
the first communication unit is configured to send the moving image captured by the imaging unit to one of the ophthalmic examination apparatuses in real time,
the second communication unit is configured to receive the moving image sent from the examination instruction apparatus, and
the controller is configured to display the moving image received by the second communication unit on the display in real time.

3. The ophthalmic examination system of claim 1, wherein
at least part of the examination optical system and at least part of the information presentation optical system share a common portion,
the display is configured to display examination information used in examination of the eye,
the projection system of the examination optical system is configured to project an examination light beam output from the display, which is displaying the examination information, onto the eye, and
when the second communication unit receives the instruction, the controller controls the display to display the instruction together with the examination information.

4. The ophthalmic examination system of claim 3, wherein the examination information includes a visual target used for visual acuity test of the eye.

5. The ophthalmic examination system of claim 2, wherein
at least part of the examination optical system and at least part of the information presentation optical system share a common portion,
the display is configured to display examination information used in examination of the eye,
the projection system of the examination optical system is configured to project an examination light beam output from the display, which is displaying the examination information, onto the eye, and
when the second communication unit receives information including at least one of the moving image and the instruction, the controller controls the display to display the information together with the examination information.

6. The ophthalmic examination system of claim 5, wherein the examination information includes a visual target used for visual acuity test of the eye.

7. The ophthalmic examination system of claim 1, wherein the controller is configured to set display size of the instruction based on at least one of visual acuity score and refractive power of the eye obtained in advance.

8. The ophthalmic examination system of claim 1, wherein the controller is configured to display at least one of text information and image information for supporting examination of the eye as the instruction.

9. The ophthalmic examination system of claim 1, wherein
each of the ophthalmic examination apparatuses further includes an audio output unit configured to output audio information, and
when the instruction includes audio information, the controller controls the audio output unit to output the audio information in real time.

10. The ophthalmic examination system of claim 1, wherein
each of the ophthalmic examination apparatuses further includes an input unit for inputting a message from a subject,
the second communication unit is configured to send the message to the examination instruction apparatus in real time,
the first communication unit is configured to receive the message sent from one of the ophthalmic examination apparatuses, and
the user interface is configured to output the message in real time.

11. The ophthalmic examination system of claim 1, wherein
each of the ophthalmic examination apparatuses further includes an information generating unit configured to generate examination status information indicating a status of examination of the eye,
the second communication unit is configured to send the examination status information to the examination instruction apparatus in real time,
the first communication unit is configured to receive the examination status information sent from the ophthalmic examination apparatus, and
the user interface is configured to output the examination status information in real time.

12. The ophthalmic examination system of claim 1, further comprising an information processing apparatus that can be used in vicinity of one of the ophthalmic examination apparatuses, wherein
the information processing apparatus includes
a communication unit configured to receive the instruction sent from the examination instruction apparatus, and
a display configured to display the instruction received by the communication unit in real time.

13. The ophthalmic examination system of claim 2, further comprising an information processing apparatus that can be used in vicinity of one of the ophthalmic examination apparatuses, wherein
the information processing apparatus includes
a communication unit configured to receive information including at least one of the moving image and the instruction sent from the examination instruction apparatus, and
a display configured to display the information received by the communication unit in real time.

* * * * *